United States Patent
Borders et al.

(10) Patent No.: US 7,138,487 B2
(45) Date of Patent: *Nov. 21, 2006

(54) EXTRACTIVE PURIFICATION OF LIPOPEPTIDE ANTIBIOTICS

(75) Inventors: Donald B. Borders, Suffern, NY (US); Noreen D. Francis, Suffern, NY (US); Amedeo A. Fantini, New City, NY (US)

(73) Assignee: Migenix Inc., Vancouver (CA)

( * ) Notice: Subject to any disclaimer, the term of this patent is extended or adjusted under 35 U.S.C. 154(b) by 6 days.

This patent is subject to a terminal disclaimer.

(21) Appl. No.: 10/810,741

(22) Filed: Mar. 26, 2004

(65) Prior Publication Data

US 2004/0242467 A1 Dec. 2, 2004

Related U.S. Application Data

(63) Continuation of application No. 09/948,374, filed on Sep. 6, 2001, now Pat. No. 6,716,962, and a continuation-in-part of application No. 09/760,328, filed on Jan. 12, 2001, now Pat. No. 6,511,962.

(60) Provisional application No. 60/286,254, filed on Apr. 24, 2001, provisional application No. 60/219,059, filed on Jul. 17, 2000, provisional application No. 60/220,950, filed on Jul. 26, 2000.

(51) Int. Cl.
*C07K 1/14* (2006.01)
*C07K 7/56* (2006.01)

(52) U.S. Cl. .......... 530/317; 530/344
(58) Field of Classification Search .......... None
See application file for complete search history.

(56) References Cited

U.S. PATENT DOCUMENTS

| | | | |
|---|---|---|---|
| 3,061,516 A | 10/1962 | Hooper et al. | 435/71.3 |
| 3,126,317 A | 3/1964 | Heinemann et al. | 424/118 |
| 3,639,582 A | 2/1972 | Umezawa et al. | 424/118 |
| 3,798,129 A | 3/1974 | Toth-Sarudy | 435/71.3 |
| 4,331,594 A | 5/1982 | Hamill et al. | 260/112.5 R |
| 4,533,631 A | 8/1985 | Kawaguchi et al. | 435/71.3 |
| 4,800,157 A | 1/1989 | Eaton et al. | 435/71 |
| 5,039,789 A | 8/1991 | Fukuda et al. | 530/317 |
| 5,912,226 A | 6/1999 | Baker et al. | 514/9 |
| 6,511,962 B1 * | 1/2003 | Borders et al. | 514/11 |
| 6,538,028 B1 * | 3/2003 | Pierson et al. | 514/564 |
| 6,624,289 B1 * | 9/2003 | Bajaj | 530/328 |
| 6,716,962 B1 * | 4/2004 | Borders et al. | 530/317 |
| 6,737,403 B1 * | 5/2004 | Borders et al. | 514/11 |
| 2002/0028771 A1 | 3/2002 | Curran et al. | 514/9 |
| 2002/0035063 A1 | 3/2002 | Borders et al. | 514/9 |
| 2005/0288222 A1 * | 12/2005 | Hayward et al. | 514/11 |

FOREIGN PATENT DOCUMENTS

| | | |
|---|---|---|
| GB | 736 325 A | 9/1955 |
| GB | 897 581 A | 5/1962 |
| WO | WO 02/05837 A | 1/2002 |
| WO | WO 02/05838 A | 1/2002 |

OTHER PUBLICATIONS

Bodanszky, M. et al., "Structure of the Peptide Antibiotic Amphomycin," *Journal of the American Chemical Society*, Apr. 4, 1973, 95(7):2352-2357.
Debono, M. et al., "Enzymatic and Chemical Modifications of Lipopeptide Antibiotic A21978C: The Synthesis and Evaluation of Daptomycin (LY146032)," *The Journal of Antibiotics*, Aug. 1988, XLI(8):1093-1105.
Martin, J.H. et al., "Isolation and Identification of D-α-Pipecolic Acid, α[L],β-Methylaspartic Acid and α,β-Diaminobutyric Acid From the Polypeptide Antibiotic Aspartocin," *Communications to the Editor*, Apr. 20, 1960, pp. 2079.
Naganawa, H. et al., "A Novel Fatty Acid From Laspartomycin," *The Journal of Antibiotics*, Aug. 1970, XXIII(8):423-424.
Naganawa, H. et al., "Laspartomycin, A New Anti-Staphylococcal Peptide," *The Journal of Antibiotics*, Jan. 1968, XXI(1):55-62.
Shay, A.J. et al., "Aspartocin. I. Production, Isolation, and Characteristics," *Antibiotics Annual*, 1959-1960, pp. 194-198.
Vertesy et al., "Friulimicins: Novel lipopopetide antibiotics with peptidoglycan synthesis inhibiting activity from Actinoplanes fiuliensis sp. nov: II. Isolation and structural characterization," *Journal of Antibiotics* 53(8): 816-827, Aug. 2000.
Borders et al., "A new chelate purification process for lipopeptide antibiotics from fermentation broths," *Abstracts Of The Interscience Conference On Antimicrobial Agents And Chemotherapy* 41:231, Sep. 2001.

* cited by examiner

*Primary Examiner*—Jeffrey Edwin Russel
(74) *Attorney, Agent, or Firm*—Darby & Darby, P.C.; Jeffrey C. Pepe

(57) ABSTRACT

The present invention provides a rapid and inexpensive method for extractively isolating acidic lipopeptide antibiotics, such as those having a cyclic peptide or cyclic depsipeptide core, in high yield and purity. In particular, there is provided a method of extracting a variety of acidic lipopeptide antibiotics, directly or indirectly, into water immiscible organic solvents by using a divalent cation chelation procedure.

16 Claims, No Drawings

EXTRACTIVE PURIFICATION OF LIPOPEPTIDE ANTIBIOTICS

CROSS-REFERENCE TO RELATED APPLICATION

This application is a continuation of U.S. patent application Ser. No. 09/948,374, filed Sep. 6, 2001, issued as U.S. Pat. No. 6,716,962 on Apr. 6, 2004, which application claims the benefit under 35 U.S.C. §119(e) of U.S. Provisional Application Ser. No. 60/286,254, filed Apr. 24, 2001 and is a continuation-in-part of U.S. patent application Ser. No. 09/760,328, filed Jan. 12, 2001, issued as U.S. Pat. No. 6,511,962 on Jan. 28, 2003, which claimed the benefit under 35 U.S.C. §119(e) of U.S. Provisional Application Ser. No. 60/219,059, filed Jul. 17, 2000 and U.S. Provisional Application Ser. No. 60/220,950, filed Jul. 26, 2000. The above applications are incorporated by reference in their entirety.

BACKGROUND OF THE INVENTION

1. Field of the Invention

The present invention relates to methods of extractively purifying and/or isolating antibiotics and/or antimicrobial agents. More particularly, the present invention relates to an inexpensive and efficient extractive method for purifying or isolating lipopeptide antibiotics.

2. Description of the Related Art

An important class of antibiotics that inhibit gram-positive bacteria are the acidic lipopeptide antibiotics. Generally, acidic lipopeptide antibiotics consist of either a cyclic peptide core or a cyclic depsipeptide core acylated with a lipophilic fragment and have an isoelectric point of less than about pH 7.0. The lipophilic fragment, typically an unsaturated fatty acid, may be of varying length. Frequently, the antibiotic activity of lipopeptide antibiotics is related to the length of the lipophilic fragment.

Examples of acidic lipopeptide antibiotics include, but are not limited to, laspartomycin (Umezawa et al., U.S. Pat. No. 3,639,582; Naganawa et al., 1968, *J. Antibiot.*, 21, 55; Naganawa et al., 1970, *J. Antibiot.*, 23, 423), zaomycin (Kuroya, 1960, *Antibiotics Ann.*, 194; Kuroya, JP 8150), crystallomycin (Gauze et al., 1957, *Antibiotiki*, 2, 9), aspartocin (Shay et al., 1960, *Antibiotics Annual*, 194; Hausman et al., 1964, *Antimicrob. Ag. Chemother.*, 352; Hausman et al., 1969, *J. Antibiot.*, 22, 207; Martin et al., 1960, *J. Am. Chem. Soc.*, 2079), amphomycin (Bodanszky et al., 1973, *J. Am. Chem. Soc.*, 95, 2352), glumamycin (Fujino et al., 1965, *Bull. Chem. Soc. Jap.*, 38, 515), brevistin (Shoji et al., 1976, *J. Antibiotics*, 29, 380), cerexin A (Shoji et al., 1976, *J. Antibiotics*, 29, 1268), cerexin B (Shoji et al., 1976, *J. Antibiotics*, 29, 1275) Antibiotic A-30912 (Hoehn et al., U.S. Pat. No. 5,039,789), Antibiotic A-1437 (Hammann et al., EP 0 629 636 BI; Lattrell et al., U.S. Pat. No. 5,629,288), Antibiotic A-54145 (Fukada et al., U.S. Pat. No. 5,039,789; Boeck et al., 1990, *J. Antibiotics*, 43, 587), Antibiotic A-21978C (Debono et al., 1988, *J. Antibiotics*, 41, 1093) and tsushimycin (Shoji et. al., 1968, *J. Antibiot.*, 21, 439). See also Berdy, "CRC Handbook of Antibiotic Compounds," Volume IV, Part I, pages 313–327, CRC Press, Boca Raton, Fla., (1980); Korzybinski et al., "Antibiotics-Origin Nature and Properties," Vol. I, Pergamon Press, pp. 397–401 and 404–408, New York, N.Y. (1967).

The acidic lipopeptide antibiotics are typically active against Gram-positive microbes and constitute important therapeutics in the treatment of infections caused by these bacteria. However, conventional procedures used to isolate and purify acidic lipopeptide antibiotics from fermentation broths involve a number of extraction and chromatography steps, which are time consuming, labor intensive and expensive to carry out on a commercial scale. Thus, there is a need in the art for improved methods of isolating and/or purifying acidic lipopeptide antibiotics.

BRIEF SUMMARY OF THE INVENTION

These and other needs are addressed by the present invention, which provides a rapid and inexpensive extractive method for purifying large quantities of lipopeptide antibiotics in high yield. Quite surprisingly, it has been discovered that acidic lipopeptide antibiotics such as laspartomycin, amphomycin and aspartocin, which have cyclic peptide nuclei and Antibiotic A-21978C, which has a cyclic depsipeptide nucleus, may under conditions of pH that are above the isoelectric point of the lipopeptide antibiotic and in the presence of divalent metal cations such as $Ca^{+2}$, be directly extracted into water-immiscible organic solvents such as 1-butanol.

While not intending to be bound by any particular theory of operation, it is believed that acidic lipopeptide antibiotics form chelates with divalent metal cations such as, for example, $Ca^{+2}$ that are stable under basic conditions and that are soluble in water-immiscible organic solvents such as 1-butanol. Under acidic conditions, the chelates are disrupted and acidic lipopeptide antibiotics may be extracted into aqueous solution at basic or near neutral pH. Thus, according to one embodiment of the invention, the method comprises contacting an aqueous composition comprising a lipopeptide antibiotic and a divalent metal cation and having a pH above the isoelectric point of the lipopeptide antibiotic with a water immiscible organic solvent, thereby extracting the lipopeptide antibiotic into organic solvent. Preferably, the pH of the aqueous composition is neutral or basic.

The lipopeptide antibiotic may then be extracted into aqueous solution from organic solvent by acidifying the organic solvent at a pH below the isoelectric point of the lipopeptide antibiotic followed by contacting the acidified organic solvent with an aqueous solution, which is at neutral or basic pH. The lipopeptide antibiotic, which now behaves like a conventional carboxylic acid, may be extracted back into organic solvent by acidifying the aqueous solution and extracting the aqueous solution with organic solvent. At this point, if necessary, the lipopeptide antibiotic may be further purified using extractive or chromatographic purification.

The extractive isolation methods of the current invention may be used to isolate and/or purity acidic lipopeptide antibiotics directly from fermentation or culture broths, either before or after removal of cells and/or cell debris and/or insoluble matter. Alternatively, the extractive isolation methods of the invention may be used in combination with conventional isolation and purification techniques. For example, an acidic lipopeptide antibiotic may be first precipitated from fermentation or culture medium and the antibiotic isolated and/or purified from the precipitate according to the extractive isolation methods of the invention. The methods of the current invention may be used to advantageously isolate and/or purify synthetic acidic lipopeptide antibiotics and/or derivatives such as the synthetic lipopeptide derivatives described, for example, in Debono et al., 1988, *J. Antibiotics*, 41, 1093 and Lattrell et al., U.S. Pat. No. 5,629,288.

Thus, when used either alone or in combination with standard extraction and chromatographic techniques, the extractive methods of the invention allow for the isolation of acidic lipopeptide antibiotics in high yield and high purity with fewer steps than are required by conventional methods.

DETAILED DESCRIPTION OF THE INVENTION

Reference will now be made in detail to preferred embodiments of the invention. While the invention will be described in conjunction with preferred embodiments, it should be understood that it is not intended to limit the invention to these preferred embodiments. To the contrary, it is intended to cover alternatives, modifications, and equivalents as may be included within the spirit and scope of the invention as defined by the appended claims.

The extractive purification methods of the invention may be used to rapidly and inexpensively isolate and/or purify virtually any acidic lipopeptide antibiotic. As used herein, "acidic lipopeptide antibiotic" refers to those antibiotics that have a cyclic peptidic nucleus with a lipophilic fragment such as a fatty acid chain attached thereto and an isoelectric point of less than about pH 7.0. The cyclic peptidic nucleus may be a cyclic peptide or a cyclic depsipeptide. The lipophilic fragment may be attached directly to the nucleus or through a linker, which is typically peptidic.

Acidic lipopeptide antibiotics may be natural products, synthetic or semisynthetic. Acidic lipopeptide antibiotics may also be derivatives of natural or synthetic acidic lipopeptide antibiotics, provided that the derivatives include carboxyl groups which permit extractive isolation according to the principles of the current invention.

Exemplary acidic lipopeptide antibiotics which can be advantageously isolated and/or purified according to the extractive methods of the invention include, but are not limited to, laspartomycin (Umezawa et al., U.S. Pat. No. 3,639,582; Naganawa et al., 1968, *J. Antibiot.*, 21, 55; Naganawa et al., 1970, *J. Antibiot.*, 23, 423), zaomycin (Kuroya, 1960, *Antibiotics Ann.*, 194; Kuroya, JP 8150), crystallomycin (Gauze et al., 1957, *Antibiotiki*, 2, 9), aspartocin (Shay et al., 1960, *Antibiotics Annual*, 194; Hausman et al., 1964, *Antimicrob. Ag. Chemother.*, 352; Hausman et al., 1969, *J. Antibiot.*, 22, 207; Martin et al., 1960, *J. Am. Chem. Soc.*, 2079), amphomycin (Bodanszky et al., 1973, *J. Am. Chem. Soc.*, 95, 2352), glumamycin (Fujino et al., 1965, *Bull. Chem. Soc. Jap.*, 38, 515), brevistin (Shoji et al., 1976, *J. Antibiotics*, 29, 380), cerexin A (Shoji et al., 1976, *J. Antibiotics*, 29, 1268), cerexin B (Shoji et al., 1976, *J. Antibiotics*, 29, 1275) Antibiotic A-30912 (Hoehn et al., U.S. Pat. No. 5,039,789), Antibiotic A-1437 (Hammann et al., EP 0 629 636 BI; Lattrell et al., U.S. Pat. No. 5,629,288), Antibiotic A-54145 (Fukada et al., U.S. Pat. No. 5,039,789; Boeck et al., 1990, *J. Antibiotics*, 43, 587), Antibiotic A-21978C (Debono et al., 1988, *J. Antibiotics*, 41, 1093) and tsushimycin (Shoji et al., 1968, *J. Antibiot.*, 21, 439). See also Berdy, "CRC Handbook of Antibiotic Compounds," Volume IV, Part 1, pages 313–327, CRC Press, Boca Raton, Fla., (1980); Korzybinski et al., "Antibiotics-Origin Nature and Properties," Vol. I, Pergamon Press, pp. 397–401 and 404–408, New York, N.Y. (1967).

Microorganisms that synthesize these various acidic lipopeptide antibiotics, as well as methods and conditions under which the microorganism may be cultured to provide the various lipopeptide antibiotics are well known in the art (see e.g., Umezawa et al., U.S. Pat. No. 3,639,582; Debono et al., 1988, *J. Antibiotics* 41: 1093; Shay et al., 1960, *Antibiotics Annual* 194; Hamill et al., U.S. Pat. No. 4,331, 594; Hamill et al., U.S. Pat. No. 4,208,403; Hoehn et al., U.S. Pat. No. 4,024,245; Higgins et al., U.S. Pat. No. 4,024,246; Boeck et al., U.S. Pat. No. 4,288,549; Boeck et al., U.S. Pat. No. 4,994,270; Boeck, U.S. Pat. No. 4,977, 083).

Those of skill in the art will appreciate that many acidic lipopeptide antibiotics are natural fermentation products comprising mixtures of isomeric compounds. The various natural product isomers differ in one or more respects, typically in the lengths, branching, and/or degree of saturation of their respective fatty acid side chains. In other instance, such as the semisynthetic lipopeptide antibiotics described in Debono et al., 1988, *J. Antibiotics*, 41, 1093 and Lattrell et al., U.S. Pat. No. 5,629,288 or those instances where natural product mixtures have been separated or where fermentation or culture conditions are controlled such that a single type of molecule is produced, acidic lipopeptide antibiotic preparations will be "pure" with respect to the antibiotic molecule (i.e., it will not comprise a mixture of molecules). It should be understood that the extractive methods of the invention may be used to isolate acidic lipopeptide antibiotics regardless of whether they constitute a mixture of molecules or a single type of molecule. However the methods of the invention do not separate different molecules of a mixture of natural fermentation products from one another. Thus, if the producing microorganism synthesizes a mixture of acidic lipopeptide antibiotics, the extractive methods of the invention may be used to isolate the mixture from other contaminants and impurities.

Acidic lipopeptide antibiotics under normal conditions are not extracted into organic solvents, even polar organic solvents, from neutral or basic aqueous solutions. Thus, when a neutral or basic aqueous solution of a acidic lipopeptide antibiotic is washed or contacted with organic solvents, the lipopeptide antibiotic typically remains in the aqueous phase, as expected for a compound that contains multiple carboxyl groups.

It has been discovered that under specified conditions, acidic lipopeptide antibiotics may be extracted into organic solvents from neutral or basic aqueous solution, which enables easy separation from acidic impurities by simple extraction. As is well known by those of skill in the art, acidic lipopeptide antibiotics may be easily separated from neutral and basic impurities by converting carboxyl groups of the antibiotic to carboxylate groups (i.e., by treating acidic lipopeptide antibiotics with base), extracting the carboxylate into aqueous solution, converting the carboxylate groups back to carboxyl groups (i.e., by treating acidic lipopeptide antibiotics with acid), and extracting the carboxyl form into organic solvent. Thus, the method of the current invention, when used in conjunction with known methods of extractively purifying lipopeptide antibiotics, enables isolation of these compounds freed from acidic, basic and neutral impurities in good yield and high purity through simple extraction, which avoids the use of expensive and time consuming chromatography steps.

The conditions which permit an acidic lipopeptide antibiotic to be partitioned or extracted into organic solvents from aqueous solution under neutral or basic conditions are related to the pH and the presence of divalent metal cation such as $Ca^{+2}$ in the aqueous solution containing the lipopeptide antibiotic. Generally, acidic lipopeptide antibiotics may be extracted into organic solvents from aqueous solutions that contain divalent metal ion, which are maintained at a pH above the isoelectric point of the antibiotics.

While not wishing to be bound by any particular theory of operation, it is believed that adjusting the pH of the solution above the isoelectric point of the acidic lipopeptide antibiotic ionizes the carboxyl groups. The carboxylate groups bind available divalent metal to form a stable divalent metal chelate of the antibiotic. The chelate, unlike the carboxylate anion of an acidic lipopeptide antibiotic, may be extracted into organic solvents from aqueous solution. Treating or washing organic solvents that contain the chelate of an acidic lipopeptide antibiotic with acid disrupts the chelate, thus providing the native acidic lipopeptide antibiotic.

Owing to this believed theory of operation, reference is made through the application to an "acidic lipopeptide antibiotic chelate." However, it will be understood that this expression is being used merely for illustration and as a means for identifying a form of acidic lipopeptide antibiotic that can be extracted into organic solvent systems, and is not intended to be limiting in any way.

Acidic lipopeptide antibiotics may be isolated and/or purified according to the invention directly from fermentation and/or culture broth, either with or without prior removal of cell debris. Alternatively, acidic lipopeptide antibiotics may first be isolated by conventional means, such as by acidic precipitation, and the precipitate resuspended and isolated and/or purified according to the extractive methods of the invention. The methods of the invention may also be used to isolate and/or purify synthetic acidic lipopeptide antibiotics and/or derivatives thereof.

As discussed above, a divalent metal cation may be chelated by ionized carboxylate groups of the acidic lipopeptide antibiotic under certain conditions. Thus, prior to extraction, the pH of the aqueous solution comprising an acidic lipopeptide antibiotic should be sufficiently basic to ionize the carboxyl groups of the lipopeptide antibiotic. Typically, the pH of the aqueous solution is adjusted to at least a pH above the isoelectric point of the particular lipopeptide antibiotic being isolated. However, as the efficiency of the extraction is believed to depend on chelate formation, the pH of the aqueous solution containing the lipopeptide antibiotic is ideally adjusted to a value that is sufficiently basic to ionize all of the carboxyl groups of the lipopeptide antibiotic (i.e., at least about pH 5.0). Preferably, the pH of the aqueous solution is between about 7.0 and about 9.0, more preferably, between about 8.0 and about 9.0 and most preferably, between about 8.5 and about 9.0. Of course, if the acidic lipopeptide antibiotic is extracted directly from fermentation or culture broth, the pH of the broth may be sufficiently basic to render further adjustments unnecessary.

In order to form an acidic lipopeptide antibiotic chelate, the aqueous solution must include a divalent metal cation. Divalent metal cations that can form chelates with acidic lipopeptide antibiotics, which may be extracted into organic solvents according to the current invention include, but are not limited to, $Ca^{+2}$, $Mg^{+2}$, $Zn^{+2}$, $Mn^{+2}$, $CU^{+2}$ and $Ni^{+2}$. Preferred divalent metal cations include $Ca^{+2}$, $Mg^{+2}$ and $Zn^{+2}$.

The amount or concentration of the divalent metal cation is not critical to success. However, since the method of the current invention is believed to operate by chelating carboxylate groups of the lipopeptide antibiotic, the molar concentration of divalent metal cation relative to the molar concentration of the acidic lipopeptide antibiotic carboxylate groups is at least about 0.5. Preferably, the molar ratio of divalent metal cation to carboxyl groups in the lipopeptide antibiotic is between about 4:1 to about 10:1. If the number of carboxyl groups in a particular acidic lipopeptide antibiotic is unknown, a desired divalent metal cation concentration and/or molar ratio may be readily determined empirically.

Divalent metal cation may be added to the aqueous solution by way of salts, and may be added before or after culturing or fermenting the producing strain, depending upon the requirement of the producing strain. The identity of the counter anion(s) is not critical; however, if the salt is added prior to culturing or fermenting the producing strain, a counter anion that negatively impacts the microorganism culture or fermentation broth should be avoided.

In many instances, the culture or fermentation broth and/or resuspended precipitate may contain a sufficient amount of divalent metal cation such that addition of further cation may be unnecessary. Whether the addition of further divalent metal cation is necessary may be determined by routine experimentation. Once the acidic lipopeptide antibiotic chelate has formed, it may be extracted into organic solvent by contacting or washing the aqueous solution comprising the chelate with organic solvent.

The organic solvent used to extract the acidic lipopeptide antibiotic chelate is not critical. However, it should satisfy two criteria: first, it should dissolve appreciable quantities of the acidic lipopeptide antibiotic chelate (i.e., the acidic lipopeptide antibiotic chelate should be more than sparingly soluble in the selected solvent system) and second, it should be at least partially immiscible with aqueous solutions (i.e., the aqueous solution and the organic solvent system should form two phases after mixing). Preferably, the organic solvent is a polar solvent in which the acidic lipopeptide antibiotic chelate is more than sparingly soluble, which is substantially immiscible with water. The organic solvent may be a pure solvent or a mixture of solvents. Suitable solvents and/or mixtures of solvents may be identified by routine experimentation. A preferred organic solvent is n-butanol.

Calculating the volume of organic solvent needed to extract the acidic lipopeptide antibiotic chelate from aqueous solution is well within the routine capabilities of skilled artisans. Typically, the volume of the organic solvent ranges about ⅓ to about 3 times the volume of the aqueous solution. Preferably, the volume of organic solvent used to extract the acidic lipopeptide antibiotic chelate from aqueous solution is about equal to the volume of the aqueous solution.

The aqueous solution may be contacted with as many portions of organic solvent necessary to extract substantially all of the acidic lipopeptide antibiotic chelate into organic solvent. The number of portions of organic solvent necessary to completely extract the acidic lipopeptide antibiotic chelate from aqueous solution (generally, at least two portions of the organic solvent will be used to extract the lipopeptide antibiotic) may be readily determined by one of skill in the art.

Generally, contacting an aqueous solution containing an acidic lipopeptide antibiotic chelate with organic solvent in a separatory funnel is sufficient to extract the acidic lipopeptide antibiotic chelate into organic solvent. However, in some situations, the organic solvent and aqueous solution may be contacted by other methods well known to the skilled artisan such, as by magnetic stirring, mechanical stirring, sonication, etc. Further, in some situations (i.e., in scale-up procedures) continuous liquid-liquid extraction may be used to extract the acidic lipopeptide antibiotic chelate into organic solvent.

The acidic lipopeptide antibiotic chelate may be disrupted by contacting organic solvent containing the chelate with acid. Preferably, the organic solvent containing the acidic lipopeptide antibiotic metal chelate is contacted with an aqueous acid solution, most preferably, with aqueous mineral acid. Ideally, the pH of the aqueous acid solution is sufficiently acidic to completely protonate the carboxylate groups of the acidic lipopeptide antibiotic chelate. Alternative methods of protonating carboxylate groups in organic solvent are known to the skilled artisan (e.g., saturating organic solvents with gaseous acids such as gaseous HCl or gaseous RBr, use of strong organic acids, etc.). Preferably, the pH of the aqueous acid solution is between about 3.0 and about 1.0, more preferably, between about 2.5 and about 1.5 and most preferably, is about 2.0. While not wishing to be bound by any particular theory of operation, it is believed that acidifying the organic phase protonates the carboxylate groups of the lipopeptide antibiotic chelate, thereby disrupting metal chelation by the carboxylic acid.

Once the organic phase containing the acidic lipopeptide antibiotic chelate has been acidified, the acidic lipopeptide antibiotic, which now behaves as a conventional carboxylic acid, may be partitioned between organic solvent and aqueous acid and base solutions by methods known to those of skill in the art. Thus, for example, the organic solvent containing the free acid of the lipopeptide antibiotic may be contacted with aqueous base solution to provide an aqueous extract of a salt of the lipopeptide antibiotic Then, treatment of the aqueous solution of the salt of the lipopeptide antibiotic with aqueous acid solution allows extraction of the free acid of the lipopeptide antibiotic into organic solvent. The free acid of the lipopeptide antibiotic after treatment with neutral or basic aqueous solution, may be again extracted into aqueous solution by conversion to the salt of the lipopeptide antibiotic. The acidic lipopeptide antibiotic may be isolated as either the salt or the free acid using methods known to the skilled artisan. The isolated acidic lipopeptide antibiotic may, if desired, be further purified by conventional methods well known to the skilled artisan such as silica gel chromatography, ion exchange chromatography, reverse phase chromatography, etc.

EXAMPLES

The invention having been described, the following examples are presented to illustrate, rather than limit, the scope of the invention. The examples illustrate various embodiments and features of the present invention.

Example 1

Selection of Parent Culture for Laspartomycin

The parent culture used for biochemical synthesis of laspartomycin is *Streptomyces viridochromogenes* ssp. *komabensis*, (ATCC-29814, BSP-M728) which was selected by the following procedure. A cell suspension of *Streptomyces viridochromogenes* ssp. *komabensis*, (ATCC-29814) was diluted so that plating on a nutrient medium gave well separated single colonies after incubation at about 28° C. A few colonies were isolated and tested by fermentation for improvement in laspartomycin yield on the basis of morphological observations (colony size, surface structure, edge profile, etc.) which are well within the capabilities of those of skill in the art. The colony BSP-M728/1, provided higher and more reproducible yields and yielded superior correlation with mycelial density in the fermentation mash. Thus, for at least these reasons, *Streptomyces viridochromogenes* ssp. *komabensis*, (ATCC-29814, BSP-M728/1) was selected for biochemical synthesis of laspartomycin.

Example 2

Medium Inoculation for Laspartomycin

Ideally, the biochemical synthesis of laspartomycin is performed by inoculating a medium composed of about 3.0% trypticase soy broth, about 1.0% corn dextrin and 0.1% $CaCO_3$ in tap water with spore and mycelial scrapings from a slant of *Streptomyces viridochromogenes* ssp. *komabensis*, (ATCC-29814, BSP-M728/1). Incubation of about 50 mL of the inoculated medium at 28° C. on a rotary shaker at about 200 revolutions per minute ("RPM") for about 48 hours provides a substantial and uniform vegetative growth. The growth may then be used to inoculate various fermentation media (See, e.g., Example 3).

Preferably, the growth comprises a concentration range of between about 2.0% to about 3.0% of the fermentation medium, when used to inoculate fermentation medium.

Example 3

Biochemical Synthesis of Laspartomycin

The inoculum produced in Example 2 may be used to seed a number of fermentation media such as: (1) a medium containing about 2.0% dextrose, about 0.5% beef extract, about 0.5% peptone, about 0.5% NaCl and about 0.35% $CaCO_3$ in water; (2) a medium containing about 0.5% dextrose, about 1.5% dextrin, about 1.0% molasses, about 1.0% peptone and about 0.1% $CaCO_3$ dissolved in water; and (3) a medium containing about 0.5% dextrose, about 1.5% glycerol, about 0.75% peptone, about 0.2% NaCl and about 0.1% $CaCO_3$ in water. In typical shaker flask fermentations, about 50 mL of the above media are seeded with the inoculum of Example 2 and are incubated at a temperature of about 28° C. on a rotary shaker at between about 160 and about 180 RPM for a period of between about 4 and about 7 days.

Example 4

Biochemical Synthesis of Laspartomycin

Biochemical synthesis of laspartomycin may be performed in a culture medium containing about 0.5% dextrose, about 1.5% corn dextrin, about 0.75% Soytone, 0.3% NaCl, about 0.1% $MgSO_4.7H_2O$ and about 0.1% $CaCO_3$ in water. The unadjusted pH of this medium is generally between about 7.2 and about 7.3. The inoculated medium is incubated at a temperature of between about 24° C. to about 34° C. (preferably between about 27° C. to about 29° C., most preferably about 28° C.) on a rotary shaker at between about 140 and about 200 RPM (preferably between about 160 and about 180 RPM) for a period of between about 4 and about 7 days (preferably, between about 5 and about 6 days) until significant amounts of laspartomycin are synthesized. Harvest pH readings of the medium are between about 8.0 and about 8.6. The yield for laspartomycin complex is about 600 mg/liter of fermentation medium, while the yield of the C-15 laspartomycin component is about 400 mg/liter of fermentation medium. The medium formulation and the quantitative ratio of its members has a direct effect on the ratio of the individual lipopeptide components of laspartomycin.

Example 5

Biochemical Synthesis of Aspartocin

The biochemical synthesis of aspartocin is performed by inoculating a medium composed of about 1.0% dextrose, 0.5% molasses, 1.0% Bacto Peptone, and 0.1% $CaCO_3$ in 100 mL of tap water, with spore and mycelial scrapings from a slant of *Streptomyces griseus* ssp. *spiralis* (NRRL B-3290; BSP-M707). The inoculated medium is incubated at a temperature of about 28° C. on a rotary shaker at about 140 rotations per minute (RPM) for about 48 hours providing a substantial and uniform vegetative growth. The latter may then be used to inoculate various fermentation media as shown below; the concentration of vegetative growth when used to inoculate a fermentation medium ranges between 2.0 and 3.0% of the fermentation medium. A number of fermentation media may be successfully employed, such as: (1) a medium containing about 2.0% dextrose, 1.0% molasses, 1.0% Bacto-Peptone, and 0.1% $CaCO_3$ in 100 mL of tap water; and (2) a medium containing about 2.0% dextrose, 0.5% Bacto-Peptone, 1.0% Maltose, and 0.1% $CaCO_3$. In a typical shaker flask fermentation, the above media are incubated at a temperature of about 28° C. on a rotary shaker at about 140 RPM for a period of between about 4 to about 7 days. Harvest pH readings are between 7.8 and 8.2.

Example 6

Biochemical Synthesis of Antibiotic A-21978

The biochemical synthesis of antibiotic complex A-21978 is performed by inoculating a culture of *Streptomyces roseosporus* (NRRL-11379; BSP-M731) in a seed medium composed of about 3.0% trypticase soy broth, and 1.0% potato dextrin in 100 mL of tap water followed by incubation at about 280 to 30° C. on a rotary shaker at about 200 RPM for approximately 48 hours. The substantial vegetative growth provided by the above procedure may then be employed to inoculate a fermentation medium in a range of 2.0 to 3.0% of the fermentation medium. A number of fermentation media may be successfully employed, but preferably one containing about 0.75% dextrose, 3.0% potato dextrin, 1.0% Soytone, 0.2% NaCl, 0.1% $MgSO_4$-$7H_2O$, and 0.25% molasses in 100 mL of tap water is used. In a typical shaker flask fermentation the above inoculated medium is incubated at a temperature of about 28° to 30° C. on a rotary shaker at about 200 RPM for a period of 4 to 7 days. Harvest pH readings range from about 6.0 to 6.5.

Example 7

Separation of Laspartomycin from Fermentation Broth Without Addition of Divalent Metal About 1.85 liters of fermentation broth produced as prepared in Example 4 (see e.g., Umezawa et al., U.S. Pat. No. 3,639,582) at pH of about 8.5 was mixed with an equal volume of 1-butanol and the phases allowed to separate. The dark brown aqueous phase was discarded and the slightly colored 1-butanol phase containing laspartomycin was combined with an equal amount of distilled water, stirred and the pH of the mixture was adjusted to about 2.0 with 1 N HCl. The 1-butanol phase was washed with ¼ its volume of water, mixed with an equal volume of water and the pH of the mixture was adjusted to about 7.0. The phases were separated and the pH of the aqueous phase containing laspartomycin was adjusted to about 2.0 and laspartomycin was extracted into 1-butanol and then back into the aqueous phase at a pH of about 7.0. The aqueous phase contained laspartomycin as the partial sodium salt. The solution was evaporated under vacuum to remove residual 1-butanol and then lyophilized to provide about 561 milligrams of the sodium salt of laspartomycin as a white powder.

Example 8

Separation of Laspartomycin from Fermentation Broth With Addition of DIY Alent Metal About 1.8 liters of fermentation broth as prepared in Example 4 (see e.g., Umezawa et al., U.S. Pat. No. 3,639,582) was adjusted to about pH 2.0 and allowed to stand at about 4° C. for three hours to precipitate laspartomycin. The cells and precipitate were isolated by centrifugation and suspended in about 500 mL of water. The pH of the suspension was adjusted to about 7.0 with 1N NaOH and the resulting mixture was stirred at room temperature for one hour. Calcium chloride (about 500 mg) was added to the suspension and the pH of the mixture was adjusted to between about 8.6 and about 9.0 with 1.0 N NaOH. Laspartomycin was extracted from aqueous solution by two sequential washes with about 500 mL and then about 100 mL of 1-butanol. The combined butanol extracts were mixed with an equal volume of distilled water, adjusted to about pH 2.0 with 1 N HCl and rinsed twice with about 200 mL of distilled water maintained at about pH 2.0. The 1-butanol phase containing the antibiotic was separated, mixed with an equal volume of distilled water and the mixture adjusted to about pH 7.0 with 1N NaOH to provide laspartomycin in the aqueous phase. The aqueous phase was separated and laspartomycin was then extracted into 1-butanol at about pH 3.0 and then into an aqueous phase at about pH 7.0. The clear, almost colorless aqueous phase was evaporated under vacuum to remove residual 1-butanol and freeze-dried to obtain 668 mg of sodium salt of laspartomycin as a white powder. High resolution FAB-MS: calculated for $C_{57}H_{90}N_{12}O_{19}$+Na $(M+Na)^+$: 1269.6343; found: 1269.6289.

Example 9

Separation of Laspartomycin from Fermentation Broth With Addition of DIY Alent Metal Calcium chloride (2.5 g) was added to 2.65 liters fermentation broth as prepared in Example 4 (see e.g., Umezawa et al., U.S. Pat. No. 3,639,582) at pH 8.7. The chelate of the laspartomycin complex was extracted with 600 mL 1-butanol (phases were separated by centrifugation). The cells and other material in an interface layer were re-extracted with another 100 mL of. 1-butanol. The 1-butanol phases were combined with 500 mL water and adjusted to pH 2.1 to remove calcium. The butanol phase, which contained laspartomycin, was washed with 100 mL water (pH 2.0), separated from the aqueous layer, and then mixed with 400 mL water adjusted to pH 7.5 to provide laspartomycin in the aqueous phase. The aqueous phase was separated, adjusted to pH 2.3 and mixed with 400 mL 1-butanol. The 1-butanol phase which, contained laspartomycin, was washed with 100 mL water (pH 2.0) and then combined with 500 mL water and adjusted to pH 7.2. The aqueous phase, which contained laspartomycin as the partial sodium salt, was evaporated to remove residual butanol and freeze-dried to obtain 1.018 g of white powder, which appeared to be about 92% pure based on HPLC area % at 215 nm. Approximately 79% of this complex was the major component, $C_{57}H_{90}N_{12}O_{19}$, at a retention time of 9.81 minutes. The minor components had retention times of 9.21 and 10.46 minutes. The HPLC system utilized a Prodigy® 5μ ODS(2) column eluted with an eight minute gradient of 10% to 75% acetonitrile at pH 7.2 with 0.05 M phosphate buffer.

Example 10

Preparation of the Acid Form of LASP Artomycin

About 100 mg of the sodium salt was prepared as described in Example 8. The sodium salt was then dissolved into about 10 mL of water, and the pH of the solution was adjusted to about 2.0 with 0.1 N HCl. Laspartomycin was then extracted into about 10 mL of 1-butanol. The 1-butanol phase was washed with about 5 mL of water, mixed with about 20 mL of water and evaporated under vacuum to obtain an aqueous solution of laspartomycin in the acid form. This solution was freeze-dried to obtain 77 mg of white powder. FAB-MS m/z:1248 $(M+H)^+$, 1270 $(M+Na)^+$ and 1286 $(M+K)^+$ indicates a molecular formula of $C_{57}H_{90}N_{12}O_{19}$ for the C-15 component of laspartomycin.

Example 11

Optimization of Calcium Concentration for Extraction of Aspartocin

The partial sodium salt of aspartocin 66 mg (~0.05 mM), was dissolved in 10 mL water to give a solution having pH 7.9. Calcium chloride, 5.5 mg (0.05 mM) dissolved in 0.11 mL water, was added along with 10 mL 1-butanol. The two phase system was shaken to equilibration. An aliquot of the 1-butanol phase, 0.25 mL, was removed for HPLC analysis. Additional 5.5 mg of calcium chloride in 0.11 mL of water was added to the two phase system which was equilibrated after each addition and analyzed by HPLC. The HPLC system utilized a Prodigy 5μ ODS (2) column eluted with an eight minute gradient of 10% to 75% acetonitrile at pH 7.2 with 0.05 phosphate buffer. The maximum extraction of the aspartocin complex occurred when the approximate molar ratio of calcium chloride/complex reached 6.

| $CaCl_2$ (mg) | approximate molar ratio* $CaCl_2$ to complex | HPLC area % at 215 nm for aspartocin complex |
|---|---|---|
| 5.5 | 1 | 36% |
| 11.0 | 2 | 71% |
| 16.5 | 3 | 88% |
| 22.0 | 4 | 92% |
| 27.5 | 5 | 89% |
| 33.0 | 6 | 100% |
| 38.5 | 7 | 99% |

*Based on a molecular weight of 1318 for major component of aspartocin and the partial sodium form of components.

Example 12

Extractive Purification of Aspartocin

Approximately 20 grams of a crude preparation of aspartocin (see e.g., Shay et al., 1960, *Antibiotics Annual*, 194), obtained by acid precipitation of fermentation broth (see Examples 5 and 8) was mixed with about 125 mL of water and insoluble impurities were separated by centrifugation. About 300 mg of $CaCl_2$ was added to the brown colored liquid and the resulting solution was adjusted to a pH of between about 8.6 to about 9.0. Aspartocin was then extracted into about 100 mL of 1-butanol. About 600 mg of $CaCl_2$ was added to the aqueous phase which was then extracted with another portion of 1-butanol. The combined butanol extracts were mixed with an equal amount of water, the pH of the mixture adjusted to about 2.0 and the butanol phase washed with about 160 mL of water adjusted to approximately pH 2.0. Aspartocin was then extracted into water at about pH 7.0 and then back into butanol at a pH of between about 2.0 to about 3.0. The butanol phase was washed with about 100 mL of water at approximately pH 2.0, then combined with an equal volume of water and adjusted to about pH 7.0. The aqueous phase is evaporated under vacuum to remove residual butanol. The very slightly colored clear liquid was freeze-dried to obtain 803 mg of the sodium salt of aspartocin as a tan-white powder. Ions of the major component by FAB-MS m/z: 1340 $(M+Na)^+$, 1384 $(M+2Na—H)^+$, 1406 $(M+3Na-2H)^+$, 1428 $(M+4Na-3H)^+$.

Example 13

Extractive Purification of Aspartocin

A dark colored crude preparation, 68.3 grams, containing 5–7% of the aspartocin complex in the acid form, was dissolved in 500 mL distilled water and stirred as the pH was adjusted to pH 7.0. Some insoluble material was separated by centrifugation and the decanted liquid was adjusted to pH 3.5. Aspartocin was extracted with two sequential 1-butanol extractions (500 mL, 300 mL) and 600 mL of water were added to the combined butanol extracts. The resulting two phase system was stirred and adjusted to pH 8.0 with 1 N NaOH to provide the aspartocin complex as the sodium salt in the aqueous phase. Calcium chloride (2.642 g) was added to the separated aqueous phase, and aspartocin extracted into 1-butanol as the chelate by two sequential extractions (500 mL, 250 mL) of 1-butanol. The 1-butanol phases were combined, mixed with 900 mL water, adjusted to pH 3.0, separated from the aqueous phase, and washed with 150 mL of water to remove calcium. The 1-butanol phase, which contained aspartocin was combined with 500 mL of water and adjusted to pH 7.0. To remove residual pigments, the aqueous phase containing the antibiotic was adjusted to pH 3.0 and mixed with 500 mL of 1-butanol. The 1-butanol phase was separated, washed with 150 mL water (pH 2–3), and combined with 500 mL water and the mixture adjusted to pH 7.0. The aqueous phase, which contained aspartocin as a partial sodium salt was evaporated under vacuum to remove residual 1-butanol and freeze-dried to obtain 3.6 g of a white powder. HPLC analysis of the purified complex showed that the aspartocin complex was approximately 90% pure by 215 nm area % with peaks of the complex ranging between 9.4 to 10.6 minutes retention time. The HPLC system utilized a Prodigy® 5μ ODS(2) column eluted with an eight minute gradient of 10% to 75% acetonitrile at pH 7.2 with 0.05 M phosphate buffer. The purified sample appeared to be approximately 98% pure by HPLC comparison to a reference sample of the aspartocin complex.

Example 14

Extractive Purification of Antibiotic A21978C

The cells from 1.9 L of fermentation broth were removed by centrifugation. The decanted liquid (1600 mL) containing approximately 204 mg of A21978C as determined by HPLC analysis was adjusted to pH 3.5 with 1 N HCl and the antibiotic extracted into 600 mL butanol. The butanol was rinsed with 100 mL distilled water maintained at pH 3.5. The 1-butanol phase containing the antibiotic was combined with 300 mL distilled water and adjusted to pH 7.3 to provide Antibiotic A-21978C in the aqueous phase. Calcium chloride (5 grams) was added to the aqueous phase and Antibiotic A-21978C chelate was extracted from the solution by two sequential extractions of about 250 mL each of 1-butanol. The combined 1-butanol extracts were mixed with an equal volume of distilled water, adjusted to pH 3.5 with 1 N HCl and rinsed with 100 mL water, pH 3.5 to remove calcium. The 1-butanol phase containing the antibiotic was separated from the aqueous phase and mixed with around 300 mL of distilled water. The pH was adjusted to 7.0 with 1 N NaOH to provide the partial sodium salt of Antibiotic A-21978C in the aqueous phase. The aqueous phase was evaporated under vacuum to remove residual 1-butanol and freeze-dried to obtain 176 mg of light tan colored powder. HPLC analysis of the purified complex showed that the A21978C was approximately 83% pure by 215 nm area % with peaks of the complex ranging between 7.9 to 9.9 minutes of retention time. The HPLC system utilized a Prodigy® 5 m ODS(2) column eluted with an eight minute gradient of 10% to 75% acetonitrile at pH 7.2 with 0.05 M phosphate buffer. The purified sample appeared to be approximately 90% pure by UV comparison to reported values of $E^{1\%}_{1\,cm}$ of the A21978 components. Found $E^{1\%}_{1\,cm}$=57 at 262 nm in EtOH, 41 at 280 nm, 36 at 290 nm and 26 at 364 nm.

Example 15

Extractive Purification of Antibiotic A-21978C

Approximately 2.0 grams of a crude brown preparation of Antibiotic A-21978C (see e.g., Debono et. al., 1988, *J. Antibiotics*, 41, 1093) obtained by 1-butanol extraction of the fermentation broth (see Example 6) was dissolved in about 150 mL water. About 1.0 grams of calcium chloride was added and the solution was adjusted to approximately pH 8.7. The lipopeptide antibiotic was then extracted into an equal volume of 1-butanol and the resulting aqueous phase was re-extracted with about 50 mL of butanol. The two butanol extractions were combined, mixed with an equal volume of water and adjusted with acid to about pH 2.0. The butanol phase was washed with about 150 mL of water at approximately pH 2.0. The lipopeptide antibiotic was then extracted into water at about pH 7.0 and then back into butanol at a pH of about 2.0 to about pH 3.0. Antibiotic A-21978C was then extracted one final time into water at approximately pH 7.0 and evaporated under vacuum to remove residual butanol. The clear yellow solution was freeze-dried to obtain 160 mg of the free acid of Antibiotic A21978C as a light-yellow/tan powder. The original aqueous phase was extracted two more times following the above procedure to provide an additional 260 mg of Antibiotic A-21978C as a light tan powder of similar quality.

While the invention has been described in some detail to facilitate understanding, it will be apparent that certain changes and modifications may be practiced within the scope of the appended claims. For example, different divalent metal ions, organic solvents, or lipopeptide antibiotics could be used in practicing the methods of the current invention. Therefore, the above described embodiments should be considered illustrative and not restrictive and the instant invention is not limited to the details given herein but may be modified within the scope of the appended claims.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for purifying a lipopeptide antibiotic, said method comprising the steps of:
   contacting an aqueous solution comprising a lipopeptide antibiotic, a divalent cation, and a pH above the isoelectric point of the lipopeptide antibiotic with an organic solvent, thereby extracting the lipopeptide antibiotic into the organic solvent, wherein the lipopeptide antibiotic is a derivative of any of the following lipopeptide antibiotics: zaomycin, crystallomycin, amphomycin, aspartocin, glumamycin, daptomycin, antibiotic A1437, antibiotic A-21978C, antibiotic A-54145 or tsushimycin, wherein the derivative is not laspartomycin; and
   contacting the organic solvent extract of the lipopeptide antibiotic with acid.

2. The method of claim 1 in which the lipopeptide antibiotic is a derivative of amphomycin.

3. The method of claim 1 in which the lipopeptide antibiotic is a derivative of aspartocin.

4. The method of claim 1 in which the lipopeptide antibiotic is a derivative of antibiotic A-21978C or a derivative of daptomycin.

5. The method of claim 1 in which the pH of the aqueous solution of the lipopeptide antibiotic is adjusted to a basic pH.

6. The method of claim 5 in which the molar concentration of divalent cation relative to carboxylate groups in the lipopeptide antibiotic is between about 4:1 and about 10:1.

7. The method of claim 5 in which the adjusted pH is in the range of about pH 8.0 to about pH 9.0.

8. The method of claim 6 in which the divalent cation is selected from the group consisting of Ca2+, Mg2+ and Zn2+.

9. The method of claim 1 further comprising:
   extracting the lipopeptide antibiotic into a third aqueous solution;
   extracting the lipopeptide antibiotic into a second organic solvent;
   extracting the lipopeptide antibiotic into a fourth aqueous solution; and
   concentrating the fourth aqueous solution to provide a salt of the lipopeptide antibiotic.

10. The method of claim 9, wherein the organic extract of the lipopeptide antibiotic is extracted into the third aqueous solution by washing with an aqueous base solution.

11. The method of claim 9, wherein the third aqueous solution of the lipopeptide antibiotic is extracted into the second organic solvent by acidifying the third aqueous solution of the lipopeptide antibiotic and contacting with the second organic solvent.

12. The method of claim 9, wherein the salt of lipopeptide antibiotic is acidified to provide a free acid of lipopeptide antibiotic.

13. The method of claim 12 in which the organic solvent and the second organic solvent is 1-butanol.

14. A method of isolating an acidic lipopeptide antibiotic, comprising the steps of:
  (a) contacting an aqueous composition comprising a lipopeptide antibiotic and a divalent metal cation with an organic solvent, wherein said aqueous composition has a pH above the isoelectric point of the lipopeptide antibiotic and the lipopeptide antibiotic is a derivative of any of the following lipopeptide antibiotics: zaomycin, crystallomycin, amphomycin, aspartocin, glumamycin, daptomycin, antibiotic A1437, antibiotic A-21978C, antibiotic A-54145 or tsushimycin, wherein the derivative is not laspartomycin;
  (b) acidifying the organic phase obtained from step (a); and
  (c) contacting the acidified organic phase of step (b) with an aqueous solvent.

15. The method of claim 14 in which steps (a) through (c) are repeated.

16. The method of claim 1 in which the organic extract of the lipopeptide antibiotic is extracted with an aqueous base solution.

* * * * *